(12) United States Patent
Sachdeva

(10) Patent No.: US 6,512,994 B1
(45) Date of Patent: Jan. 28, 2003

(54) METHOD AND APPARATUS FOR PRODUCING A THREE-DIMENSIONAL DIGITAL MODEL OF AN ORTHODONTIC PATIENT

(75) Inventor: Rohit Sachdeva, Plano, TX (US)

(73) Assignee: OraMetrix, Inc., Dallas, TX (US)

(*) Notice: Subject to any disclaimer, the term of this patent is extended or adjusted under 35 U.S.C. 154(b) by 0 days.

(21) Appl. No.: 09/560,641

(22) Filed: Apr. 28, 2000

Related U.S. Application Data

(63) Continuation-in-part of application No. 09/452,034, filed on Nov. 30, 1999.

(51) Int. Cl.[7] ................................................. A61D 3/00
(52) U.S. Cl. .......................... 702/167; 433/24; 433/29
(58) Field of Search .............................. 702/152, 153, 702/155, 166, 167; 433/24, 29, 215, 3, 11, 20; 382/120; 345/672; 700/182

(56) References Cited

U.S. PATENT DOCUMENTS

| | | | |
|---|---|---|---|
| 4,575,805 A | 3/1986 | Moermann et al. | 700/163 |
| 4,837,732 A | 6/1989 | Brandestini et al. | 433/29 |
| 5,011,405 A | 4/1991 | Lemchen | 433/24 |
| 5,238,404 A | 8/1993 | Andreiko | 433/20 |
| 5,338,198 A | 8/1994 | Wu et al. | 433/213 |
| 5,368,478 A | 11/1994 | Andreiko et al. | 433/24 |
| 5,372,502 A | 12/1994 | Massen et al. | 433/215 |
| 5,395,238 A | 3/1995 | Andreiko et al. | 433/24 |
| 5,424,836 A | 6/1995 | Weise et al. | 356/602 |
| 5,431,562 A | 7/1995 | Andreiko et al. | 433/24 |
| 5,447,432 A | 9/1995 | Andreiko et al. | 433/24 |
| 5,454,717 A | 10/1995 | Andreiko et al. | 433/24 |
| 5,456,600 A | 10/1995 | Andreiko et al. | 433/24 |

(List continued on next page.)

FOREIGN PATENT DOCUMENTS

| | | |
|---|---|---|
| DE | 0250 993 | 6/1987 |
| DE | 44 45 552 | 6/1995 |
| DE | 196 36 354 | 3/1998 |
| DE | 196 38 727 | 3/1998 |
| DE | 196 38 758 | 3/1998 |

OTHER PUBLICATIONS

Syrinx, Bending Robot.
Syrinx, Orthotherm.
Syrinx, 3D Scanner.
S.M. Yamany and A.A. Farag, "A System for Human Jaw Modeling Using Intra–Oral Images" in *Proc. IEEE Eng. Med. Biol. Soc. (EMBS) Conf.*, vol. 20, Hong Kong, Oct. 1998, pp. 563–566.
S.M. Yamany, A.A. Farag, David Tasman, A.G. Farman, "A 3–D Reconstruction System for the Human Jaw Using a Sequence of Optical Images," *IEEE Transactions on Medical Imaging*, vol. 19, No. 5, May 2000, pp. 538–547.
Co–pending patent application of Rohit Sachdeva, Ser. No. 09/452,034, filed Nov. 30, 1999.
U.S. patent application Ser. No. 09/452,034 filed on Nov. 30, 1999.

*Primary Examiner*—Kamini Shah
*Assistant Examiner*—John Le
(74) *Attorney, Agent, or Firm*—McDonnell Boehnen Hulbert & Berghoff

(57) ABSTRACT

A method and apparatus for producing a three-dimensional digital model of an orthodontic patient include processing that begins by obtaining data of an orthodontic structure of the orthodontic patient. The processing then continues by obtaining at least one scaling reference point of the orthodontic structure. The processing continues by scaling the data of the orthodontic structure based on the at least one scaling reference point to produce scaled data. The process then continues by obtaining at least two orientation reference points relating to the orthodontic structure. The processing then continues by mapping the scaled data to a coordinate system based on the at least two orientation reference points to produce the three-dimensional digital model of the orthodontic patient.

27 Claims, 7 Drawing Sheets

U.S. PATENT DOCUMENTS

| | | | |
|---|---|---|---|
| 5,464,349 A | 11/1995 | Andreiko et al. | 433/24 |
| 5,474,448 A | 12/1995 | Andreiko et al. | 433/24 |
| RE35,169 E | 3/1996 | Lemchen et al. | 433/24 |
| 5,518,397 A | 5/1996 | Andreiko et al. | 433/24 |
| 5,533,895 A | 7/1996 | Andreiko et al. | 433/24 |
| 5,542,842 A | 8/1996 | Andreiko et al. | 433/3 |
| 5,604,817 A | 2/1997 | Massen et al. | 382/120 |
| 5,618,176 A | 4/1997 | Andreiko et al. | 433/11 |
| 5,715,166 A | 2/1998 | Besl et al. | 700/182 |
| 5,742,294 A | 4/1998 | Watanabe et al. | 345/672 |
| 5,879,158 A | 3/1999 | Doyle et al. | 433/24 |
| 5,975,893 A | 11/1999 | Chishti et al. | 433/6 |
| 6,068,482 A | 5/2000 | Snow | 433/223 |
| 6,099,314 A | 8/2000 | Kopelman et al. | 433/213 |
| 6,217,325 B1 | 4/2001 | Chishti et al. | 433/24 |
| 6,227,850 B1 | 5/2001 | Chishti et al. | 433/24 |
| 6,227,851 B1 | 5/2001 | Chishti et al. | 433/24 |

FIG. 1A
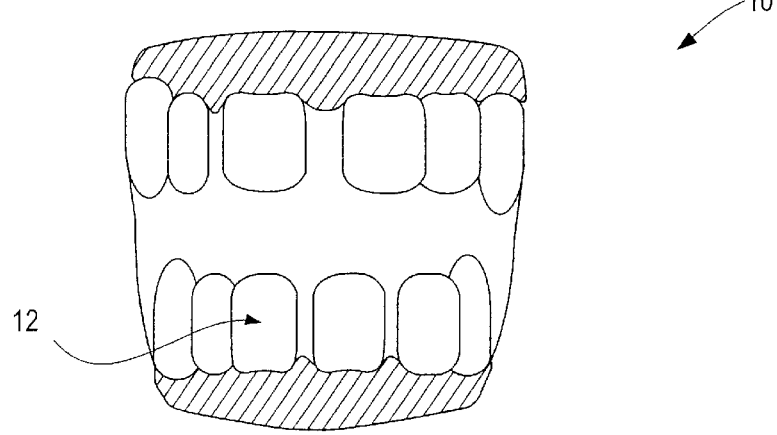
FIG. 1B
FIG. 1C
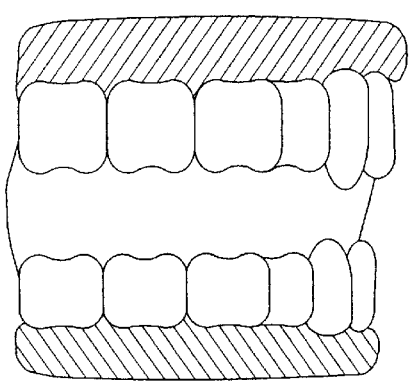
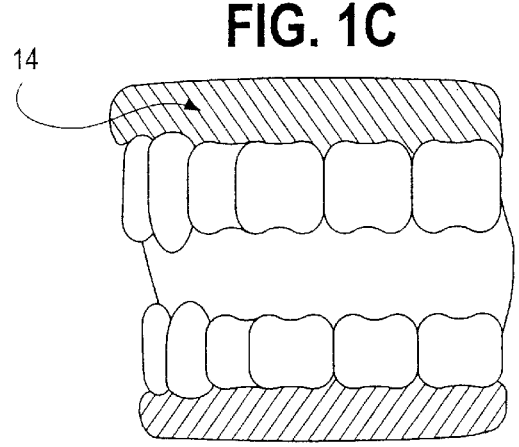
FIG. 1D
FIG. 1E
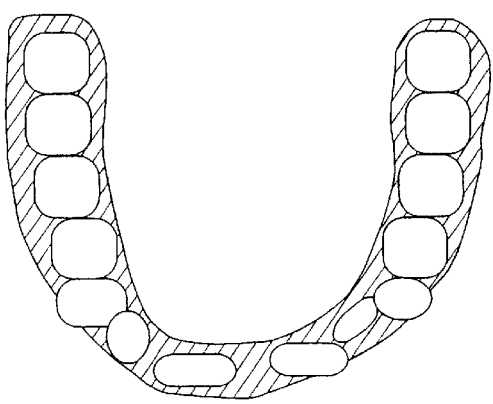
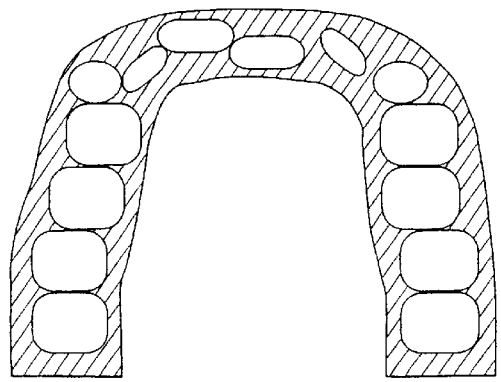

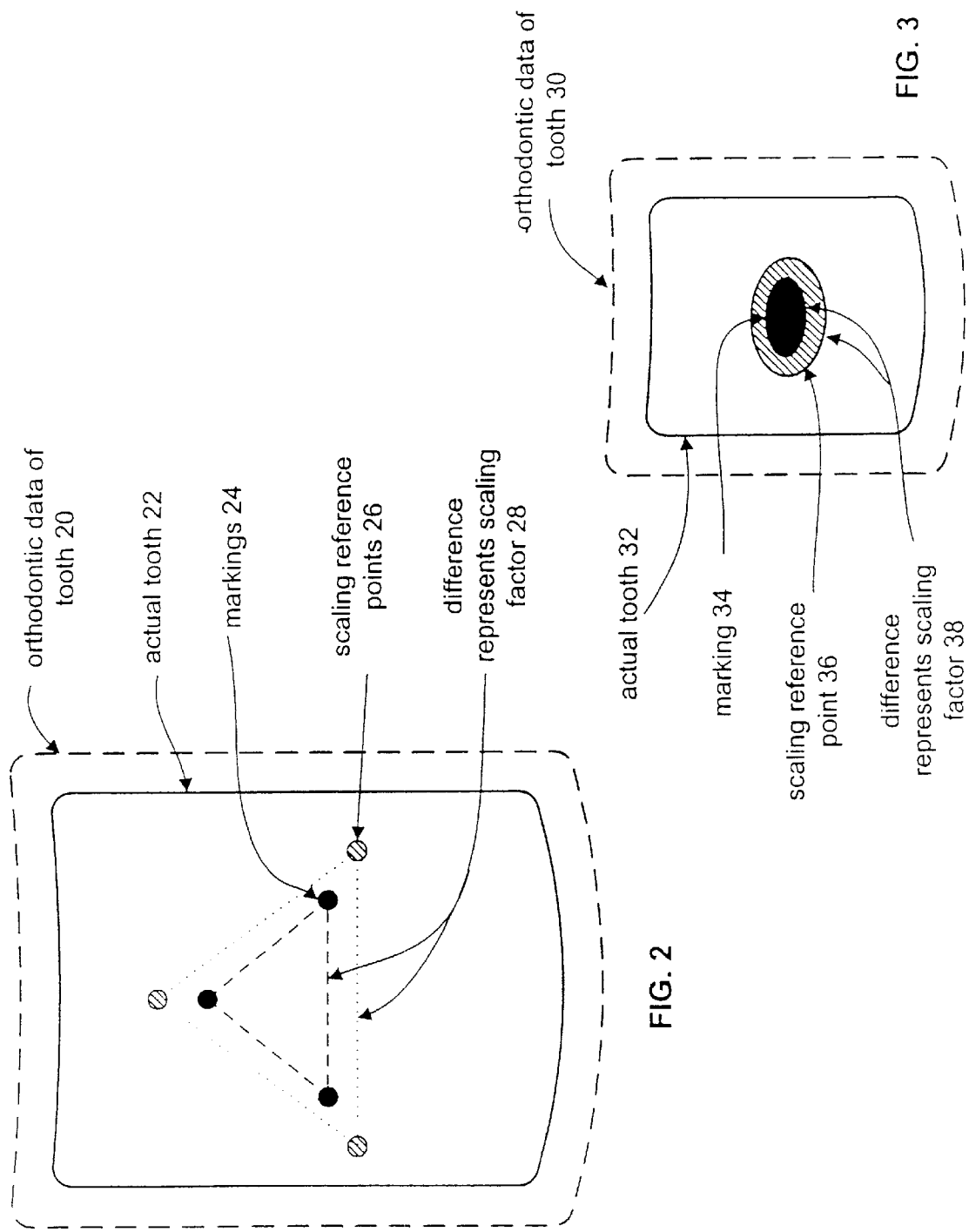

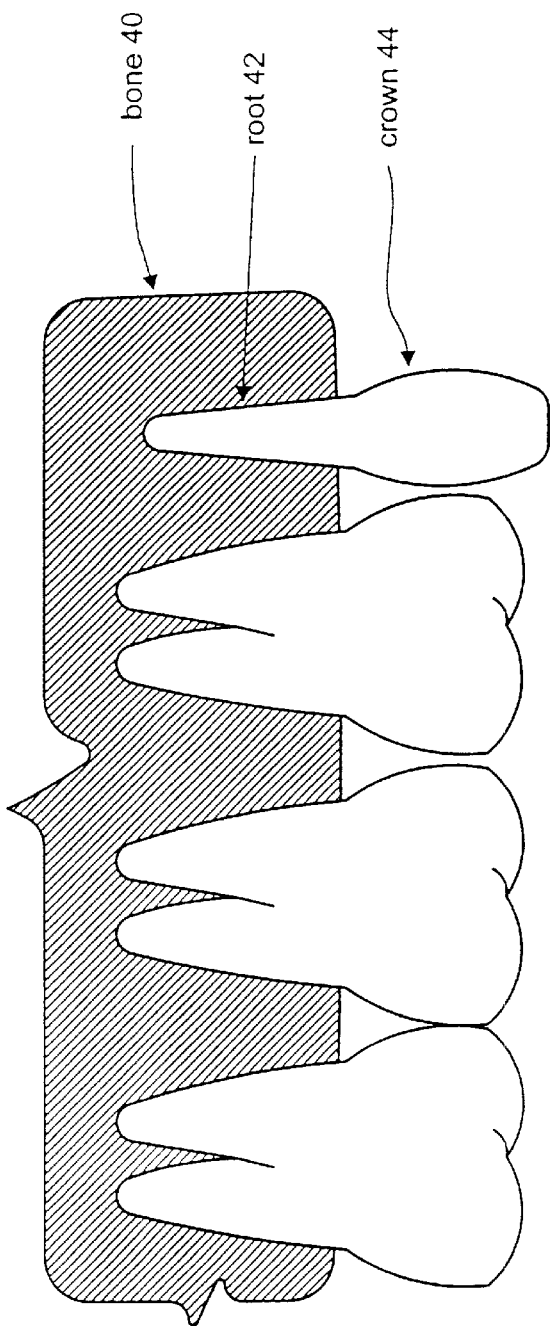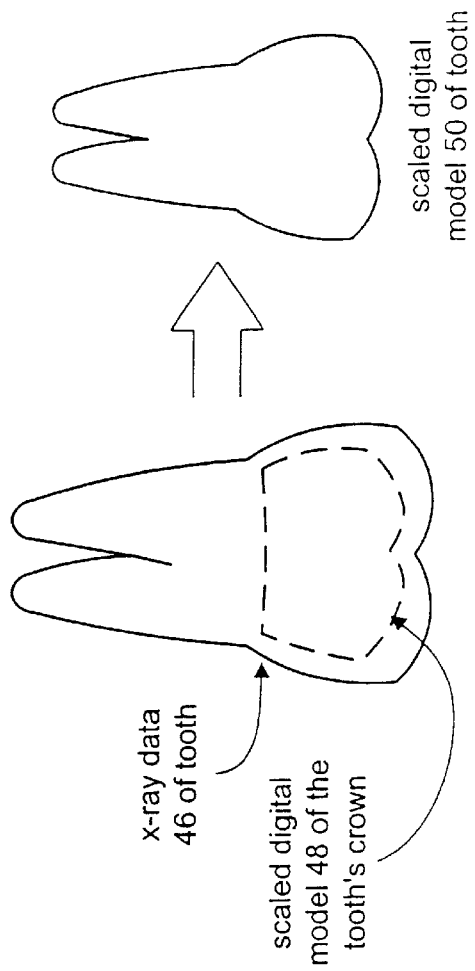

METHOD AND APPARATUS FOR PRODUCING A THREE-DIMENSIONAL DIGITAL MODEL OF AN ORTHODONTIC PATIENT

CROSS-REFERENCE TO RELATED APPLICATION

This is a continuation-in-part of Ser. No. 09/452,034, filed Nov. 30, 1999.

TECHNICAL FIELD OF THE INVENTION

This invention relates generally to the practice of orthodontics and in particular to a method and apparatus for treating an orthodontic patient.

BACKGROUND OF THE INVENTION

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth ,to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Unfortunately, the current innovations to change the practice of orthodontic from an art to a science have only made limited progress. This limit is due to, but not restricted to, the brackets being the focal point for orthodontic manipulation. By having the brackets as the focal point, placement of each bracket on a corresponding tooth is critical. Since each bracket includes a custom sized and positioned wire retaining groove, a misplacement of a bracket by a small amount (e.g., an error vector having a magnitude of millimeter or less and an angle of a few degrees or less) can cause a different force system (i.e., magnitude of movement and direction of movement) than the desired force system to be applied to the tooth. As such, the tooth will not be repositioned to the desired location.

Another issue with the brackets being the focal point is that once the brackets are placed on the teeth, they are generally fixed for the entire treatment. As such, if the treatment is not progressing as originally calculated, the orthodontist uses his or her expertise to make the appropriate changes. The treatment may not progress as originally calculated for several reasons. For example, misplacement of a bracket, misapplication of a bend in the wire, loss or attrition of a bracket, bonding failure, the patient falls outside of the "normal" patient model (e.g., poor growth, anatomical constraints, etc.), patient lack of cooperation in use of auxiliary appliance, etc. are factors in delayed treatment results. When one of these conditions arise, the orthodontist utilizes his or her expertise to apply manual bends to the wire to "correct" the errors in treatment. Thus, after the original scientific design of the brackets, the practice of the orthodontic converts back to an art for many patients for the remainder of the treatment.

Another issue with the brackets being the focal point is that customized brackets are expensive. A customized bracket is produced by milling a piece of metal (e.g., stainless steel, aluminum, ceramic, titanium, etc.) and tumble polishing the milled bracket. While the milling process is very accurate, some of the accuracy is lost by tumble polishing. Further accuracy is lost in that the placement of the brackets on the teeth and installation of the wire are imprecise operations. As is known, a slight misplacement of one bracket changes the force on multiple teeth and hinders treatment. To assist in the placement of the custom brackets, they are usually shipped to the orthodontist in an installation jig. Such an installation jig is also expensive. Thus, such scientific orthodontic treatment is expensive and has many inherent inaccuracies.

Therefore, a need exists for a method and apparatus that provides a scientific approach to orthodontics throughout the treatment, maintains treatment costs, and provides a three-dimensional digital model of an orthodontic patient.

BRIEF DESCRIPTION OF THE DRAWINGS

FIGS. 1A–1E illustrate a graphical diagram of orthodontic data in accordance with the present invention;

FIG. 2 illustrates a graphical diagram of scaling in accordance with the present invention;

FIG. 3 illustrates a graphical diagram of an alternate scaling approach in accordance with the present invention;

FIG. 4 illustrates a graphical diagram of x-rayed teeth in accordance with the present invention;

FIG. 5 illustrates a graphical diagram of scaling the x-rayed tooth in accordance with the present invention;

DETAILED DESCRIPTION OF A PREFERRED EMBODIMENT

Figure 6A:
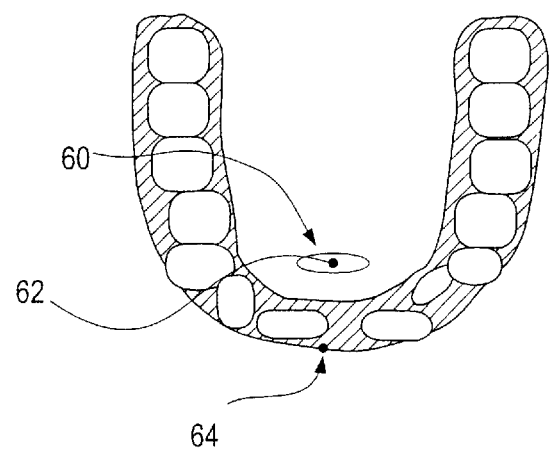
FIGS. 6A–6C illustrate a graphical representation of determining orientation reference points in accordance with the present invention.

Generally, the present invention provides a method and apparatus for producing a three-dimensional digital model of an orthodontic patient. Such a method and apparatus include processing that begins by obtaining data of an orthodontic structure of the orthodontic patient. The processing then continues by obtaining at least one scaling reference point of the orthodontic structure. For example, the scaling reference point may be a marking placed on a tooth prior to obtaining the data. The processing continues by scaling the data of the orthodontic structure based on the at least one scaling reference point to produce scaled data. Note that the data may be video data, x-rays, CAT scans, ultrasound, and/or magnetic resonance images. The process then continues by obtaining at least two orientation reference points relating to the orthodontic structure (i.e., fixed physical attributes of the orthodontic structure that will not change, or will change with negligible effects, during the course of treatment). The processing then continues by mapping the scaled data to a coordinate system based on the at least two orientation reference points to produce an enhanced three-dimensional digital model of the orthodontic patient. With such a method and apparatus, the automated treatment of an orthodontic patient occurs in a scientific and controlled manner. By obtaining an accurate three-dimensional digital model that includes a dentition structure of the orthodontic patient, patient treatment can be simulated by a computer in three-dimensional space, thereby providing a scientific approach to orthodontic treatment.

The present invention can be more fully described with reference to FIGS. 1 through 9. FIGS. 1A–1E illustrate various views of a graphical representation of orthodontic data 10 of the orthodontic structure of an orthodontic patient. In essence, the orthodontic data is scan data representing a three-dimensional graphic surface image of the patient's teeth, gums, lips, and other surfaces of the facial area. The orthodontic data shown in FIGS. 1A–1E only includes the teeth 12 and gums 14. As one of average skill in the art will appreciate, the surfaces may also include lips, cheeks, chin, nose, etc. The orthodontic data may be obtained by scanning a patient's mouth to obtain video data thereof. The scanning may be done utilizing a laser scanner, light scanner, ultrasound, MRI, CAT scan, or other scanning technique, such as the scanning technique, such as the scanning technique disclosed in patent application Ser. No. 09/560,584, filed on Apr. 28, 2000, which is hereby incorporated herein by reference. Note that the light scanner approach may be directly performed on the patient while a laser scanner and other scanning techniques are typically done on a plaster model. Regardless of the scanning technique, three-dimensional images of the surface of the orthodontic structure are obtained.

FIG. 2 illustrates a graphical representation of scaling the orthodontic data to match the actual orthodontic size. Depending on of the scanning technique, the orthodontic data will not completely reproduce the exact size of the teeth and other portions of the orthodontic structure. To facilitate the accuracy of the three-dimensional digital model, at least one tooth 22 can be marked utilizing markings 24. The marking is done prior to obtaining the orthodontic data. Once the orthodontic data for the tooth 20 is obtained, the scaling reference points 26 are also obtained. A determination between the differences between the scaling reference points 26 and the actual markings 24 determine a scaling factor 28. As one of average skill in the art will readily appreciate, having the actual markings 24 and the scaling reference points 26, a variety of mathematical operations may be used to determine the scaling factor. For example, the differences in area formed by the triangles may be used to generate the scaling factor, the coordinate differences between each of the vertices of the triangle may be utilized. As one of average skill in the art will further appreciate, a different number of markings 24 may be utilized. For example, two markings may be used or four markings may be used, etc. In addition, more than one tooth may be marked with similar markings 24. Note that the markings may be on the exterior of the patient, and a local triangulation technique may be used to obtain the scaling factor. Further note that the scaling factor 28 determination is based on an assumption that the video data 10 will have a linear error term in each of the x, y and z axis, such that a single scaling factor is determined and used to scale each of the teeth as well as the other aspects of the orthodontic structure of the patient. Such scaling will be discussed with reference to FIGS. 4–9.

FIG. 3 illustrates an alternate marking technique for determining a scaling factor for the orthodontic data. As shown, an actual tooth 32 is marked with a marking 34. The marking 34 is of a substantial size to be adequately measured. Once the orthodontic data is obtained, the orthodontic data of the tooth 30 and a corresponding scaling reference point 36 are used to determine the scaling factor 38. As one of average skill in the art will readily appreciate, a simple mathematical function may be used to determine the scaling factor 38 based on the size difference between the actual marking 34 and the scaling reference point 36. As an alternative to marking as described with reference to FIGS. 2 and 3, the actual tooth size may be measured and used to determine the scaling factor. Accordingly, the difference between the actual tooth size the size of the tooth in the video data 10 will constitute the scaling factor.

When three-dimensional scanning of the type described in application Ser. No. 09/560,584 is used, scaling of the three-dimensional data is not needed as a true three-dimensional image is obtained through the use of triangulation. Likewise, a true three-dimensional image can be obtained by x-ray techniques such as computed tomography.

FIG. 4 illustrates a two-dimensional representation of image data, such as a graphical diagram of a radiographic image, such as an x-ray of a few teeth. In another embodiment, the radiographic image can be a computed tomographic image volume. As previously mentioned, the orthodontic data contains three-dimensional images of the surface of the orthodontic structure. X-rays provide a more detailed view of the teeth and surrounding hard and soft tissue as two dimensional image data. As shown in FIG. 4, each tooth includes a crown 44 and a root 42 and is embedded in bone 40. Accordingly, the orthodontic data only illustrates the crown 44 of the teeth. As such, the three-dimensional model of the orthodontic patient requires the roots and bone to be included. Note that the X-ray image can include addition facial and/or cranial features other than those illustrated or described.

FIG. 5 illustrates a graphical representation of using the scaled digital model 48 of the tooth's crown to produce an integrated or composite digital model 50 of the tooth. In this embodiment, the x-rayed data 46 of the tooth is used in comparison with the scaled digital model to determine a per tooth scaling factor. The scaled digital model 48 of the tooth is positioned to be planar with the x-ray of the tooth 46. Having obtained the proper orientation between the two objects, the per tooth scaling factor is determined and subsequently used to generate the composite scaled digital model 50 of the tooth. In a specific embodiment, the per tooth scaling factor is required for current x-ray technologies, since x-rays produce a varying amount of distortion from tooth to tooth depending on the distance of the tooth from the film, the angle of x-ray transmission, etc.

To more accurately map the two-dimensional images of a tooth on to the three-dimensional model, multiple angles of the tooth should be used. Accordingly, a side, a front, and a bottom view of the tooth should be taken and mapped to the scaled digital model of the tooth. Note that the bone and other portions of the orthodontic structure are scaled in a similar manner. Further note that MRI images, and any other images obtained of the orthodontic patient, may also be scaled in a similar manner.

Figure 6B:
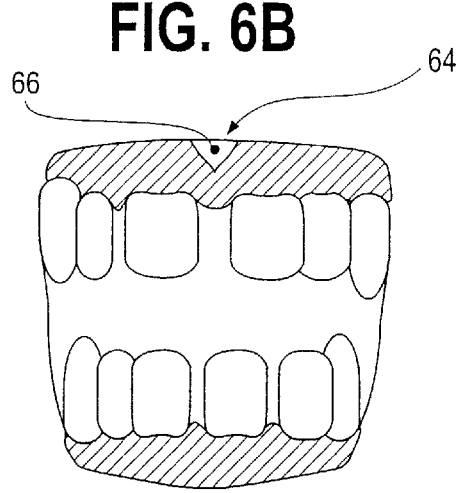
Figure 6C:
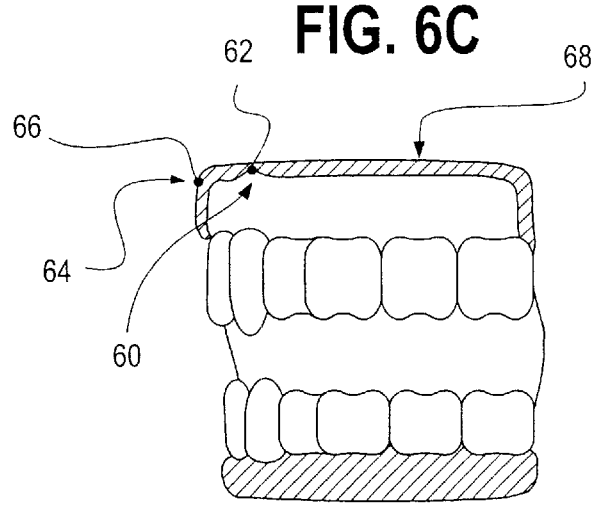

FIGS. 6A–6C illustrate a graphical diagram of selecting orientation reference points based on physical attributes of the orthodontic structure. The orientation reference points 62 and 66 will be subsequently used to map the digital image of the orthodontic structure into a three-dimensional coordinate system that will not change during the course of treatment. In this example, the frenum 64 has been selected to be one of the orientation reference points 66 and the rugae 60 has been selected as the other reference point 62. The frenum 64 is a fixed point in the orthodontic patient that will not change, or change minimally, during the course of treatment. As shown, the frenum is a triangular shaped tissue in the upper-portion of the gum of the upper-arch. The rugae 60 is a cavity in the roof of the mouth 68 in the upper-arch. The rugae will also not change its physical position through treatment. As such, the frenum 64 and the rugae 60 are fixed physical points in the orthodontic patient that will not change during treatment. As such, by utilizing these as the orientation reference points 62 and 66, a three-dimensional coordinate system may be mapped thereto. Note that other physical attributes of the orthodontic patient may be used as the orientation reference points 62 and 66. However, such physical points need to remain constant throughout treatment. Accordingly, alternate physical points include the incisive papilla, cupid's bow, the inter-pupillar midpoint, inter-comissural midpoint (e.g., between the lips), inter-alar midpoint (e.g., between the sides of the nose), the prone nasale (e.g., the tip of the nose), sub-nasale (e.g., junction of the nose and the lip), a dental mid-line point, a point on the bone, a fixed bone marker such as an implant (e.g., a screw from a root canal, oral surgery).

The x, y, z coordinate system may be mapped to the physical points on the digital module of the orthodontic structure in a variety of ways. In one example, the origin of the x, y, z coordinate system may be placed at the frenum 64, the z-axis aligned with reference to the frenum and the rugae 60, and the x-axis is aligned with the midline of the upper and/or lower arch. This is further illustrated in FIGS. 7 and 8. Note that an external positioning system may be used to obtain the orientation reference points. For example, the patient may sit in a chair at a specific location of an examination room that includes a triangulation positioning system therein. As such, when the patient is scanned, the scanned images may be referenced with respect to the room's triangulation positioning system.

Figure 7:
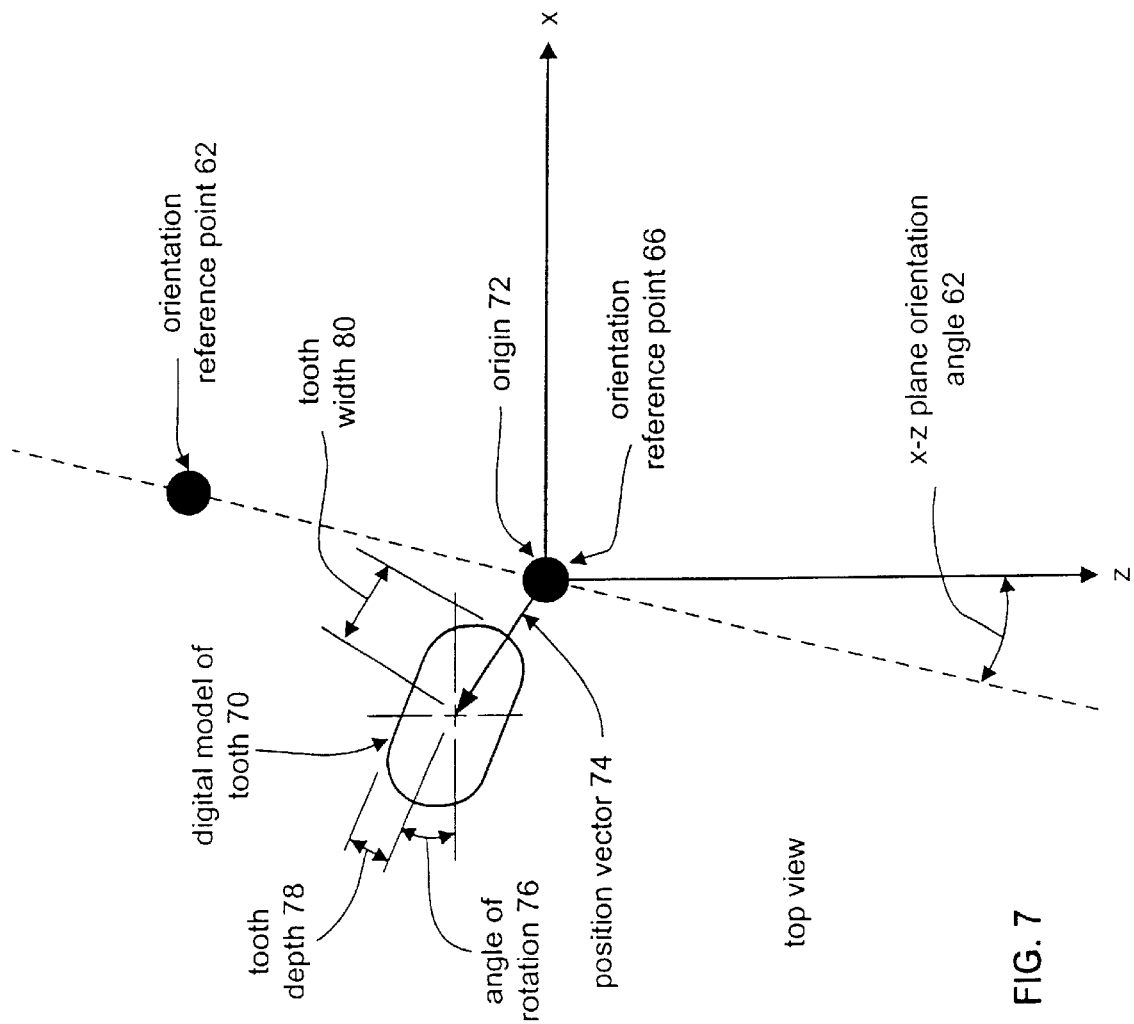
FIGS. 7 and 8 illustrate a graphical representation of mapping the orientation reference points to a three-dimensional coordinate system in accordance with the present invention.

FIG. 7 illustrates a graphical representation of mapping the orientation reference points 62 and 66 to the x-z plane of the three-dimensional x, y, z coordinate system. In this illustration, orientation point 66, which corresponds to the frenum 64, is selected as the origin of the x, y, z coordinate system. Note that any location may be selected as the origin 72. The orientation points 62 and 66 are used to determine an x, z plane orientation angle 62. Typically, the x, y, z coordinate system will be selected such that when looking at the patient from a frontal view, the x direction will be to right of the patient, the y direction towards the top of the patient's head and the z direction will be out away from the patient. As one of average skill in the art will appreciate, the orientation of the x, y, z plane may be in any orientation with respect to the reference points 62 and 66.

Figure 8:
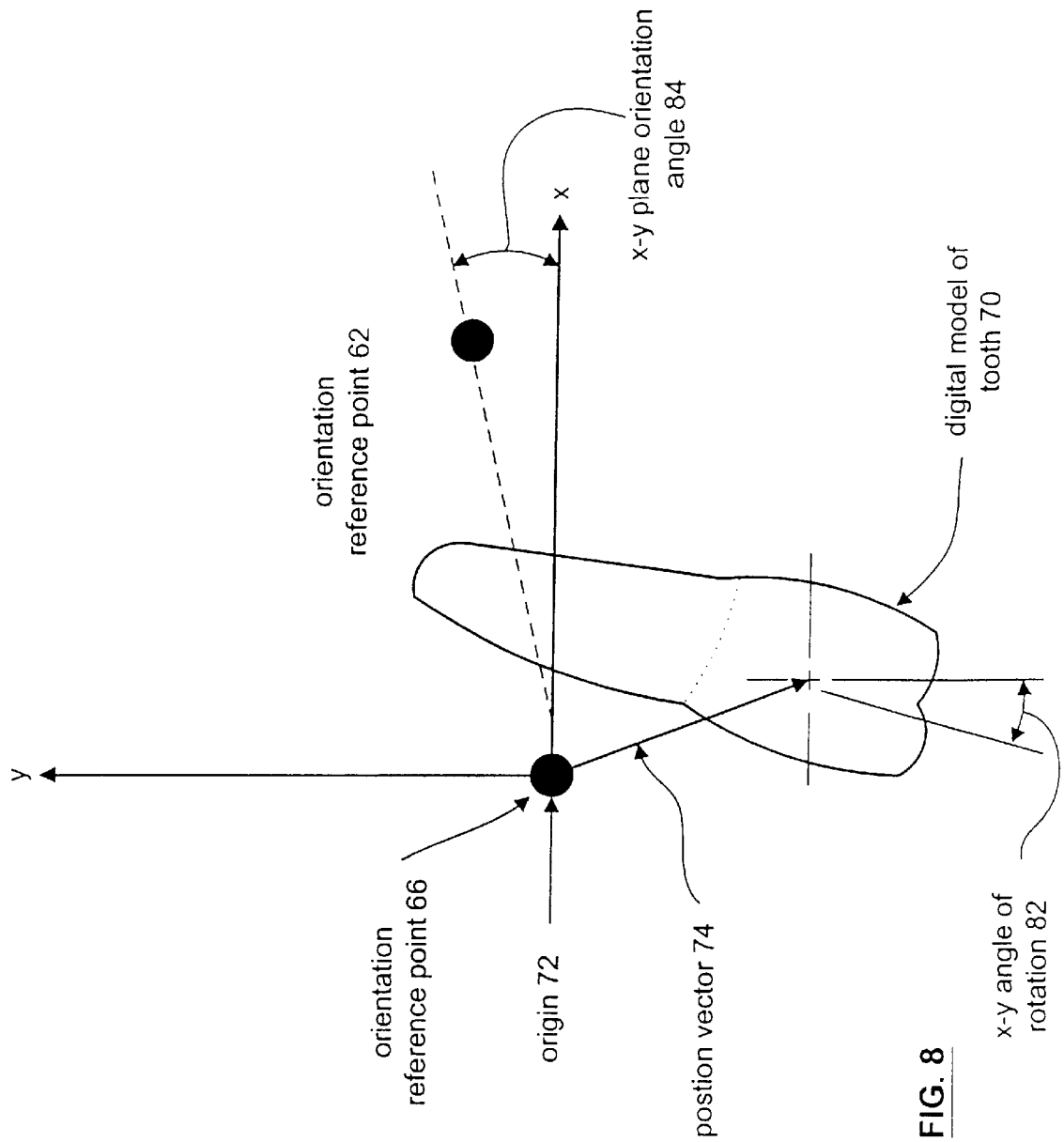

The x-y plane is mapped to the orientation reference point 62 and 66 as shown in FIG. 8. The orientation reference point 62 and 66 are used to generate an x-y plane orientation angle 84. Based on the x-y plane orientation angle 84 and the x-z plane orientation angle 62, a digital model of a tooth 70 may be positioned in three-dimensional space with respect to the x, y, z coordinate system. As shown in FIGS. 7 and 8, the digital model of the tooth 70 includes a tooth depth 78, an angle of rotation 76 with respect to the x-z axis, an angle of rotation 82 with respect to the x-y plane, a positioning vector 74 which is in a three-dimensional space, the length of the tooth including the crown dimension, and the root dimension. Accordingly, each tooth is then mapped into the x, y, z coordinate system based on the tooth's center, or any other point of the tooth, and the dimensions of the digital model of the corresponding tooth. Once each tooth has been placed into the x, y, z coordinate system, the digital model of the tooth is complete. Note that the lower-arch is also referenced to the x, y, z coordinate system wherein the determination is made based on the occlusal plane of the patient's orthodontic structure. Alternatively, the lower-arch may include a separate three-dimensional coordinate system that is mapped to the coordinate system of the upper-arch. In this latter example, fixed points within the lower-arch would need to be determined to produce the lower arches three-dimensional coordinate system.

Figure 9:
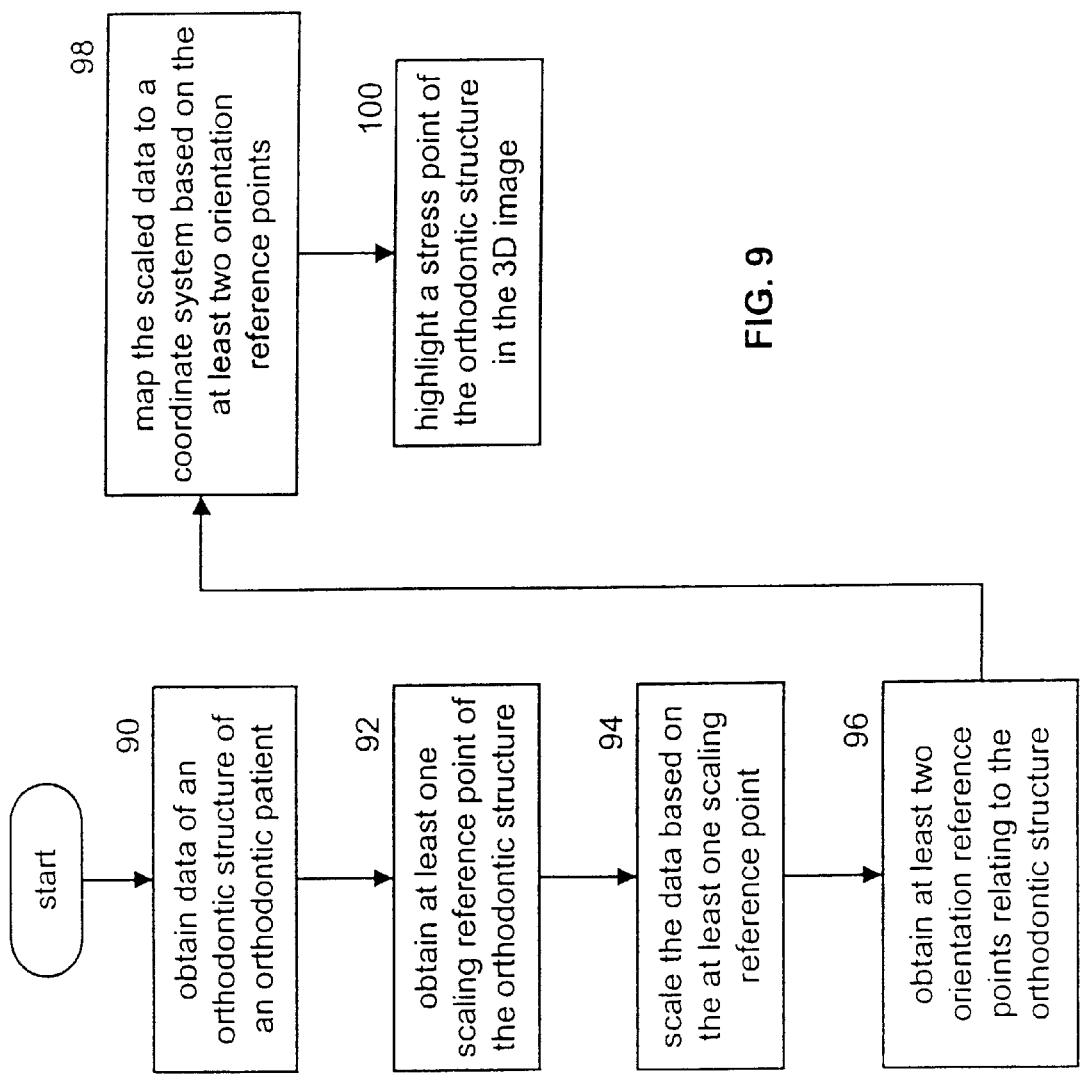
FIG. 9 illustrates a logic diagram of a method for producing a three-dimensional digital model of an orthodontic patient in accordance with the present invention.

FIG. 9 illustrates a logic diagram of a method for producing a three-dimensional digital model of an orthodontic patient. The processing steps of FIG. 9 may be implemented as operational instructions that are stored in memory and executed by a processing module. For example, the processing module and memory may be of the type found in the orthodontic server as described in co-pending patent application, which is hereby incorporated by reference, having Ser. No. 09/560,643, entitled METHOD AND APPARATUS FOR DETERMINING AND MONITORING ORTHODONTIC TREATMENT, a filing date the same as the present application, and is assigned to the same assignee as the present patent application.

The process begins at step 90 where orthodontic data of an orthodontic structure of an orthodontic patient is obtained. In essence, the orthodontic data includes a three-dimensional graphical surface image of the orthodontic structure, which may be obtained as video data using a light scanner, laser scanner, ultra sound scanner, and/or other scanning device. The orthodontic data may further include two dimensional data such as x-rays, MRIs, CAT scans, photographs, etc. In addition to obtaining images of the orthodontic structure, the system may obtain color information of the teeth and surrounding soft tissue to use as texture information for the three-dimensional object. Note that the three-dimensional surface image which may be obtained as video data, includes information regarding the teeth surface, gum surface, lips surface and facial surface. Further note that the video data may be dynamic motion of the orthodontic structure which will be later used to determine appropriate functionality of the orthodontic structure.

The process then proceeds to step 92 where at least one scaling reference point of the orthodontic structure is obtained. This may be done by marking at least two points on one or more teeth via a jig, marking a tooth with a known shape via a jig, measuring at least two anatomical points, identifying at least two points on a true three-dimensional model, and/or measuring physical dimensions of a tooth.

The process then proceeds to step 94 where the data is scaled based on the at least one scaling reference. To begin the scaling process, as described with reference to FIGS. 1 through 8, the surface data, which may be obtained as video data, is scaled first. Once the video data has been scaled, x-rays and/or photographs may be scaled in accordance with the scaled video data. For x-rays, the scaling must be done on a tooth by tooth basis by orientating the scaled video data on a tooth by tooth basis such that the digital module of the tooth surface is substantially planer with the two-dimensional x-ray, MRI, etc. of a given tooth. Having done this, a scaling factor is determined for the given tooth based on the planer scaled video data and the two-dimensional image. The two-dimensional imagery of the tooth (i.e., root and crown) is then scaled based on the scaling factor to produce a scaled tooth. This was illustrated with respect to FIG. 5. Note that regardless of whether the data contains scanned images that were obtained via an MRI process, infrared process, CAT scan, ultrasound, and/or laser scan, such images are scaled in accordance with the scaled video data.

In a specific embodiment, by knowing the parameters used to capture the two-dimensional image the scaling needed to orient the two-dimensional image a three-dimensional model can be reduced by changing the virtual orientation of the three-dimensional model to match the two dimensional view. In this manner, the scaling is done by manipulating the three dimensional model. Additional fine tuning of the three-dimensional model orientation can be subsequently performed to achieve a best fit. In this manner, any dentition points that can be clearly recognized and defined in both the three-dimensional image and the two-dimensional image (e.g. incisor edges, cusps, etc.) can be used to align the images.

The process then proceeds to step 96 where at least two orientation reference points that relate to the orthodontic structure are obtained. These reference points may be applied by a practitioner, or local care provider, and may include the mid-point frenum, incisive papilla, rugae, cupid's bow, inter-pupillar midpoint, inter-comissural midpoint, inter-alar midpoint, prone nasale, sub-nasale, dental mid-line point, a fixed point on a bone, a fixed bone marker such as implants that resulted from a root canal, oral surgery, etc. In addition, facial features may be used as the reference points, which include the ear, lateral aspect of the face, the bottom of the chin, the nose, etc.

The process then proceeds to step 98 where the scaled data is mapped to a coordinate system based on the at least two reference points. This was discussed with reference to FIGS. 7 and 8. Note that, if the orthodontic data includes a motion picture of the orthodontic structure, the moving lower arch is mapped to the coordinate system to obtain functional accuracy of the orthodontic structure. In addition, the movement of the jaw, and hence the orthodontic structure, can be determined by including the bone portions related to the jaw using the techniques described herein. This allows a simulation using the integrated simulation model to determine alignment and position of the lower jaw. Therefore, modifications to the location of dentition structures in a digital model can be simulated using movement of the jaw to determine if the planned location of the dentition structures is appropriate, or if additional modification of the model will create a better result.

The process then proceeds to step 100 where at least one stress point of the orthodontic structure is highlighted. The stress point could be within the jaw, mouth or anywhere in the head and is determined based on contact between at least one upper-tooth and lower-tooth of the orthodontic structure. The stress point is subsequently used to determine a desired orthodontic structure as discussed in co-pending patent application, which is hereby incorporated by reference, having Ser. No. 09/560,134, entitled METHOD AND APPARATUS FOR GENERATING A DESIRED THREE-DIMENSIONAL DIGITAL MODEL OF AN IDEAL ORTHODONTIC STRUCTURE, having a filing date the same as the present patent application, and is assigned to the same assignee as the present patent application.

Using an iterative method in accordance with the present invention is advantageous over prior methods that were ultimately based upon a single two-dimensional analysis. By using a three-dimensional model in accordance with a specific embodiment of the present invention in conjunction with an iterative process, any factor that effects tooth movement (i.e. brackets, wires, adhesion, physiological changes) can be simulated to determine appropriate treatment changes. Such compensation in treatment is not possible using prior methods which were based upon assumptions from a single model that the tooth movement would progress in a known manner. Therefore, the prior art methods would specify and a single static treatment based upon this assumption. If any unwanted tooth movement occurred during treatment, the specified treatment would no longer be valid, requiring changes to be made based upon a practitioner's expertise. The present system provides a dynamic system that through the use of periodic feedback, i.e. periodic three-dimensional scanning, can be monitored and adjusted as needed by the system in an efficient manner. As such, unexpected tooth movement, such as occurs when a patient does not cooperate, or through biological changes, can be readily The preceding discussion has presented a method and apparatus for producing a three-dimensional digital model of an orthodontic patient. By generating a digital model of an orthodontic patient, a scientific approach to orthodontic treatment may be obtained in a closed-looped system. As one of average skill in the art would readily appreciate, other embodiments may be derived from the teaching of the present invention without deviating from the scope of the claims.

What is claimed is:

1. A method for producing a three-dimensional digital model of an orthodontic patient, the method comprises the steps of:
   a) obtaining data of an orthodontic structure of the orthodontic patient;
   b) obtaining at least one scaling reference point of the orthodontic structure;
   c) scaling the data of the orthodontic structure based on the at least one scaling reference point to produce scaled data;
   d) obtaining at least two orientation reference points relating to the orthodontic structure;
   e) mapping the scaled data to a coordinate system based on the at least two orientation reference points to produce the three-dimensional digital model.

2. The method of claim 1 further comprises obtaining the data to be at least one of: two-dimensional imagery of the orthodontic structure and video data.

3. The method of claim 2 further comprises:
   scaling the video data based on the at least one scaling reference point to produce scaled video data; and
   scaling the two-dimensional imagery based on the scaled video data.

4. The method of claim 3 further comprises, on a tooth by tooth basis,
   orientating the scaled video data for a given tooth to be substantially planar with the two-dimensional imagery of the given tooth;
   obtaining a scaling factor for the given tooth based on the planar scaled video data and the two-dimensional imagery; and
   scaling the two-dimensional imagery of the given tooth based on the scaling factor to produce a scaled tooth.

5. The method of claim 4, wherein step (e) further comprises:
   mapping the scaled teeth to the coordinate system based on the at least two orientation reference points; and
   integrating the scaled teeth and the scaled video data to produce the three-dimensional digital model.

6. The method of claim 5, wherein the three-dimensional digital model includes a combination of at least two of: three-dimensional digital model of the teeth and roots, gums, bones, and soft tissue.

7. The method of claim 1, wherein step (a) further comprises obtaining color of the teeth and soft tissue of the orthodontic structure within the video data; and
   wherein step (e) further comprises producing the three-dimensional digital model having substantially true color the teeth and the soft tissue.

8. The method of claim 1, wherein step (b) further comprises obtaining the at least one scaling reference point by at least one of: marking at least two points on one or more teeth via a jig, marking a tooth with a known shape via a jig, measuring at least two anatomical points, and measuring physically dimensions of a tooth.

9. The method of claim 8 further comprises:
   obtaining reference video data of the orthodontic structure including the at least one scaling reference;
   comparing the reference video data with the video data to obtain a scaling factor; and
   scaling the video data based on the scaling factor to produce the scaled video data.

10. The method of claim 1, wherein step (d) further comprises obtaining the at least two orientation points.via inputs from a practitioner.

11. The method of claim 1, wherein step (a) further comprises obtaining teeth surface information, gum surface information, lip surface information, and facial surface information as the video data.

12. The method of claim 1, wherein step (a) further comprises obtaining dynamic motion of the orthodontic structure within the video data; and
   wherein step (e) further comprises mapping upper plate information of the orthodontic structure with lower plate information of the orthodontic structure based on the dynamic motion.

13. The method of claim 1, wherein step (e) further comprises highlighting a stress point of the orthodontic structure within the three-dimensional digital model, wherein the stress point is determined based on contact between upper teeth of the orthodontic structure and lower teeth of the orthodontic structure.

14. The method of claim 1, wherein step (a) further comprises obtaining a three-dimensional imagery of the orthodontic structure.

15. The method of claim 14 further comprises:
   scaling the three-dimensional imagery based on the scaled video data to produce scaled three-dimensional imagery; and
   wherein step (e) further comprises mapping the scaled three-dimensional imagery to the coordinate system and integrating the scaled video data with the scaled three-dimensional imagery to produce the three-dimensional digital model.

16. An apparatus for producing a three-dimensional digital model of an orthodontic patient, the apparatus comprises:
   a processing module; and
   memory operably coupled to the processing module, wherein the memory includes operational instructions that cause the processing module to: (a) obtain data of an orthodontic structure of the orthodontic patient; (b) obtain at least one scaling reference point of the orthodontic structure; (c) scale the data of the orthodontic structure based on the at least one scaling reference point to produce scaled data; (d) obtain at least two orientation reference points relating to the orthodontic structure; (e) map the scaled data to a coordinate system based on the at least two orientation reference points to produce the three-dimensional digital model.

17. The apparatus of claim 16, wherein the memory further comprises operational instructions that cause: the processing module to:

highlight a stress point of the orthodontic structure within the three-dimensional digital model, wherein the stress point is determined based on contact between upper teeth of the orthodontic structure and lower teeth of the orthodontic structure.

18. The apparatus of claim 16, wherein the memory further comprises operational instructions that cause the processing module to obtain, as the data, at least one of: two-dimensional imagery of the orthodontic structure and video data.

19. The apparatus of claim 18, wherein the memory further comprises operational instructions that cause the processing module to:

scale the video data based on the at least one scaling reference point to produce scaled video data; and scale the two-dimensional imagery based on the scaled video data.

20. The apparatus of claim 19, wherein the memory further comprises operational instructions that cause the processing module to, on a tooth by tooth basis, orientate the scaled video data for a given tooth to be substantially planar with the two-dimensional imagery of the given tooth;

obtain a scaling factor for the given tooth based on the planar scaled video data and the two-dimensional imagery; and scale the two-dimensional imagery of the given tooth based on the scaling factor to produce a scaled tooth.

21. The apparatus of claim 20, wherein the memory further comprises operational instructions that cause the processing module to:

map the scaled teeth to the coordinate system based on the at least two orientation reference points; and integrate the scaled teeth and the scaled video data to produce the three-dimensional digital model.

22. The apparatus of claim 21, wherein the three-dimensional digital model includes a combination of at least two of: three-dimensional digital model of the teeth and roots, gums, bones, and soft tissue.

23. The apparatus of claim 16, wherein the memory further comprises operational instructions that cause the processing module to:

obtain color of the teeth and soft tissue of the orthodontic structure within the video data; and produce the three-dimensional digital model having substantially true color the teeth and the soft tissue.

24. The apparatus of claim 16, wherein the memory further comprises operational instructions that cause the processing module to obtain the at least one scaling reference point by at least one of: marking at least two points on one or more teeth via a jig, marking a tooth with a known shape via a jig, measuring at least two anatomical points, and measuring physically dimensions of a tooth.

25. The apparatus of claim 24, wherein the memory further comprises operational instructions that cause the processing module to:

obtain reference video data of the orthodontic structure including the at least one scaling reference;

compare the reference video data with the video data to obtain a scaling factor; and scale the video data based on the scaling factor to produce the scaled video data.

26. The apparatus of claim 16, wherein the memory further comprises operational instructions that cause the processing module to obtain teeth surface information, gum surface information, lip surface information, and facial surface information as the video data.

27. The apparatus of claim 16, wherein the memory further comprises operational instructions that cause the processing module to:

obtain dynamic motion of the orthodontic structure within the video data; and map upper plate information of the orthodontic structure with lower plate information of the orthodontic structure based on the dynamic motion.

* * * * *